United States Patent [19]

Harrison et al.

[11] Patent Number: 5,426,207
[45] Date of Patent: Jun. 20, 1995

[54] CONTINUOUS PRODUCTION PROCESS OF DIARYLCARBONATES

[75] Inventors: George E. Harrison, Billericay; Alan J. Dennis; Mohammad Sharif, both of Middlesbrough, all of United Kingdom

[73] Assignee: Davy Research and Development Limited, Cleveland, England

[21] Appl. No.: 142,125

[22] Filed: Oct. 28, 1993

[51] Int. Cl.$^6$ ............................................. C07C 69/96
[52] U.S. Cl. ................................................... 558/274
[58] Field of Search ....................................... 558/274

[56] References Cited

U.S. PATENT DOCUMENTS

| | | |
|---|---|---|
| 4,045,464 | 8/1977 | Romano et al. . |
| 4,182,726 | 1/1980 | Illuminati et al. . |
| 4,410,464 | 10/1983 | Hallgren . |
| 4,609,501 | 9/1986 | Mark . |
| 5,210,268 | 5/1993 | Fukuoka et al. ............ 558/270 |

FOREIGN PATENT DOCUMENTS

| | | |
|---|---|---|
| 461274 | 12/1991 | European Pat. Off. . |
| 3308921 | 9/1983 | Germany . |
| 18458 | 10/1992 | WIPO . |

OTHER PUBLICATIONS

J. L. R. Williams et al., *J. Org. Chem.*, 24(1), pp. 64–69 (1959).

Primary Examiner—Mary C. Lee
Assistant Examiner—M. G. Ambrose
Attorney, Agent, or Firm—Rothwell, Figg, Ernst & Kurz

[57] ABSTRACT

A diaryl carbonate is produced by transesterification of a dialkyl carbonate, such as dimethyl carbonate, with an aromatic hydroxy compound, such as phenol, in three successive reaction zones. A transesterification catalyst, such as a titanate ester or ester mixture is used in each zone. Conditions are selected to maximize formation of alkyl aryl carbonate in the first and second reaction zones, while conversion to diaryl carbonate is favored in the third reaction zone. The vaporous mixture from the first two reaction zones is a mixture containing alkyl alcohol, dialkyl carbonate, alkyl aryl carbonate and aromatic hydroxy compound. This mixture is separated in an alkyl alcohol recovery zone by distillation in the distillation columns to produce useful recycle streams. The second of these distillation columns can be operated at a lower pressure than the first, thus enabling the heat of vaporization of this mixture to be used as the source of heat for the reboiler of the second distillation column of the alkyl alcohol recovery zone.

21 Claims, 2 Drawing Sheets

CONTINUOUS PRODUCTION PROCESS OF DIARYLCARBONATES

This invention relates to a process for the production of aromatic carbonates, such as diphenyl carbonate.

Aromatic carbonates are employed commercially as intermediates in the production of aromatic polycarbonates and also in the production of some isocyanates. They can be prepared from the corresponding phenol by a reaction involving use of phosgene or a chloroformate in the presence of an acid binding agent, such as an organic base or an inorganic alkali, for example sodium hydroxide or sodium carbonate. However, it would be desirable to avoid use of phosgene due to its toxicity.

Production of di-aryl carbonates from the corresponding aryl alkyl carbonates with simultaneous formation of a dialkyl carbonate is described in U.S. Pat. No.4,045,464. This reaction is carried out in the presence of a titanium tetraphenate or titanium tetramethylate.

U.S. Pat. No.4,182,726 describes preparation of diaryl carbonates and aryl alkyl carbonates by reacting a phenol or an acyl ester thereof with an alkyl, cyclic or aryl-alkyl carbonate in the presence of a catalyst, such as $AlCl_3$.

Use of a catalyst which is a physical admixture of a Lewis acid and a protic acid in the production of aliphatic aromatic carbonates by reaction of a phenolic compound and a dialiphatic carbonate is described in U.S. Pat. No.4,609,501.

The production of a diaromatic carbonate can be exemplified by the production of diphenyl carbonate by reaction of phenol with dimethyl carbonate. This involves the following chemical equations:

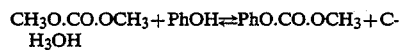

$$CH_3O.CO.OCH_3 + PhOH \rightleftharpoons PhO.CO.OCH_3 + CH_3OH \quad (1);$$

and

$$PhO.CO.OCH_3 + PhOH \rightleftharpoons (PhO)_2CO + CH_3OH \quad (2).$$

These reactions can be summarised thus:

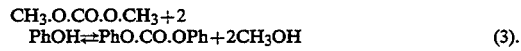

$$CH_3.O.CO.O.CH_3 + 2 PhOH \rightleftharpoons PhO.CO.OPh + 2CH_3OH \quad (3).$$

Another competing reaction is the disproportionation of methyl phenyl carbonate according to the following equation:

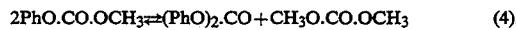

$$2PhO.CO.OCH_3 \rightleftharpoons (PhO)_2.CO + CH_3O.CO.OCH_3 \quad (4).$$

An investigation of reactions of the type exemplified by equation (4) is described in the article "Disproportionation of Unsymmetrical Carbonates" by J. L. R. Williams et al., J.Org. Chem., 24(1), pages 64 to 68 (1959). This article discloses how mixed ethyl and aryl or aralkyl carbonates disproportionate when heated with suitable catalysts to yield diethyl carbonate and the corresponding other symmetrical carbonate. Catalysts investigated include sodium methoxide, titanium tetrachloride, titanium butoxide, strontium methoxide, magnesium methoxide, aluminium isopropoxide, tetraethyl tin, lead borate, and sodium phenoxide. Titanium butoxide is reported to be the catalyst of choice.

It is possible to measure the equilibrium constants for the reactions of equations (1) to (4). Typical results are as follows:

| Reaction No. | $K_c$ value |
|---|---|
| (1) | $2.6 \times 10^{-3}$ |
| (2) | $6.2 \times 10^{-4}$ |
| (3) | $1.61 \times 10^{-7}$ |
| (4) | $2.35 \times 10^{-1}$ |

It is evident from inspection of the above values that a small concentration of reactant methanol in the reaction medium will inhibit the formation of significant concentrations of diphenyl carbonate in reaction solutions. Results which support this statement are reported in J. L. R. Williams et al., loc.cit., who used a solution of strontium methoxide in methanol and a mixture of $LiAlH_4$ and ethanol in separate experiments and stated: "The odor of phenol was noted in both cases" (see page 65, loc. cit.) Hence the reaction analogous to equation (1) above is a significant factor in this system.

The prior art lacks a commercial process which can be operated continuously to produce di-aryl carbonates, such as diphenyl carbonate, in an efficient manner, starting from the corresponding optionally substituted phenol, or other monocyclic aromatic hydroxy compound, which avoids the use of the toxic chemical phosgene.

The present invention accordingly seeks to provide a continuous process for the production of di-aryl carbonates which uses the corresponding phenol, or other aromatic hydroxy compound, which obviates the use of phosgene, and which can be practised successfully on a commercial scale.

According to the present invention a continuous process for the production of a di-aryl carbonate comprises:

(a) providing a plurality of reaction zones including a primary reaction zone, a secondary reaction zone, and a tertiary reaction zone;

(b) supplying to the primary reaction zone a dialkyl carbonate and an aromatic hydroxy compound;

(c) maintaining the primary reaction zone under reaction conditions conducive to formation of the corresponding alkyl aryl carbonate;

(d) reacting the dialkyl carbonate and the aromatic hydroxy compound together in the primary reaction zone in the presence of a transesterification catalyst;

(e) recovering from the primary reaction zone a vaporous stream comprising alkyl alcohol and a liquid stream comprising alkyl aryl carbonate and depleted in alkyl alcohol;

(f) maintaining the secondary reaction zone under reaction conditions conducive to formation of the corresponding alkyl aryl carbonate;

(g) reacting material of the liquid stream of step (e) in the secondary reaction zone with further aromatic hydroxy compound in the presence of a transesterification catalyst to produce further alkyl aryl carbonate;

(h) recovering from the secondary reaction zone a substantially alkanol-free liquid bottom stream containing alkyl aryl carbonate and excess aromatic hydroxy compound and an overhead vaporous stream;

(i) passing material of the bottom stream of step (h) to the tertiary reaction zone;

(j) maintaining the tertiary reaction zone under temperature and pressure conditions conducive to formation of diaryl carbonate by disproportionation of alkyl aryl carbonate; and (k) recovering from the tertiary reaction zone a liquid bottom product containing diaryl carbonate and a vaporous overhead stream comprising aromatic hydroxy compound and dialkyl carbonate.

Suitable transesterification catalysts for use in the process of the present invention include Lewis acids, salts, and esters of transition metals, organic and inorganic borates, and mixtures thereof. As examples thereof there can be mentioned in particular titanate esters of the formula $Ti(OX)_4$, where X is alkyl or aryl, such as tetraalkyl titanates, tetraaryl titanates, mixed alkyl/aryl titanates, and mixtures thereof. In such titantes alkyl groups are preferably n-alkyl groups and contain typically from 1 to about 20 carbon atoms, whilst aryl groups are typically monocylic or bicyclic aryl groups which may bear one or more substituents, such as chloro, nitro or alkoxy groups. Specific examples include tetraphenyl titanate, tetra-(iso-nonylphenyl) titanate, tetramethyl titanate, tetraethyl titanate, tetra-n-propyl titanate, tetra-n-butyl titanate, tetra-n-hexyl titanate, tetra-n-decyl titanate, tetralauryl titanate, tetratetradecyl titanate, tetrahexadecyl titanate, tetraeicosyl titanate, tri-n-propyl n-butyl titanate, di-n-propyl di-n-butyl titanate, n-propyl tri-n-butyl titanate, lauryl triphenyl titanate, dilauryl diphenyl titanate, trilauryl phenyl titanate, lauryl tri-(iso-nonylphenyl)titanate, dilauryl di-iso-nonylphenyl titanate, trilauryl iso-nonylphenyl titanate, and the like, and mixtures thereof. Other transesterification catalysts include aluminium compounds, uranium compounds, zinc compounds, vanadium compounds, ferric compounds, and tin compounds. Examples include compounds of the formula $AlY_3$, $UY_4$, $ZnY_2$, $VOY_3$, $VY_5$, $FeY_3$ and $SnY_4$, where Y represents chlorine, bromine, alkoxy containing from 1 to about 20 carbon atoms, or aryloxy wherein aryl is a monocyclic or bicyclic aryl group such as phenyl, p-nitrophenyl, o-chlorophenyl or α-naphthyl. Organic and inorganic borates that may be used as transesterification catalyst include compounds of the formula $B(OX)_3$, where X is alkyl or aryl, and inorganic borates such as lead borate.

Typical transesterification conditions include use of a temperature of from about 25° C. to about 350° C., a pressure of from about 0.1 bar up to about 100 bar and a transesterification catalyst concentration in the range of from about 5 ppm up to about 1000 ppm by weight measured as metal (or, in the case of borates, as boron). Within these temperature and pressure ranges the conditions are selected such that the desired components of the various vaporous streams have a significant vapour pressure and such that an acceptable rate of reaction can be achieved at the selected catalyst concentration, thereby permitting a tolerable throughput to be achieved. The space velocity through the primary reaction zone may differ from that prevailing in the secondary reaction zone whilst the space velocity through the tertiary reaction zone may in turn differ from that prevailing in the primary reaction zone and/or in the secondary reaction zone. Expressed as a liquid hourly space velocity, the space velocity through each reaction zone preferably lies in the range of from about 0.1 hr$^{-1}$ up to about 10.0 hr$^{-1}$; if the material is in fact supplied in vapour form to a reaction zone, then it is necessary to calculate the equivalent space velocity for that material as if it were supplied in liquid form. The selection of suitable transesterification conditions is within the competence of any skilled chemical engineer who has access to the relevant vapour pressure data and binary pair vapour/liquid equilibrium data for the reactants, intermediate products, by-products, and products at different temperatures, as well as to reaction rate data. Preferably the operating conditions in each reaction zone, such as pressure, temperature and space velocity, are selected so that the volume flow rates of the various recycle streams containing intermediate products and reactants are minimised so far as possible. Much of the relevant information required for selecting optimum conditions has been published in the technical literature; if not, it can readily be determined by standard methods.

In the course of the transesterification reactions which take place in the process of the invention the nature of the radicals X or Y in the transesterification catalyst may change with time due to exchange with alkoxy groups derived from the alkyl alcohol formed as a co-product and/or with aryloxy groups derived from the aromatic hydroxy compound used as starting material. Hence the active catalytic species may change with time from the catalyst precursor supplied to the respective reaction zone. For example, if the aromatic hydroxy compound is phenol and the dialkyl carbonate is dimethyl carbonate, then although a tetraalkyl titanate such as a tetra-n-butyl titanate may be supplied to the respective reaction zone, the actual catalytic species may in time become $(MeO)_x(PhO)_yTi$, where each of x and y is zero or an integer of from 1 to 4 and x+y equals 4. Hence the actual catalytic species may tend to become tetraphenyl titanate formed as a result of an ester interchange reaction between phenol and the tetra-n-butyl titanate catalyst precursor. Any n-butanol produced as a result of such ester interchange reactions is usually recovered in the vaporous overhead stream from the respective reaction zone. In this context it should also be mentioned that, because of the ready interchange of alkoxy and aryloxy groups around the titanium atom of the catalytic species, a high boiling phenol or alcohol, e.g. iso-nonylphenol or n-hexadecanol, can be added to the reaction medium in small amounts. Such added small amounts have the effect of lowering the melting point of any catalyst-containing residue recovered in operation of the process of the invention and hence facilitates catalyst recyling. Hence it contemplated to add to the liquid transesterification medium, when using a titanium ester as transesterification catalyst, a higher boiling hydroxy compound, such as a substituted phenol, an optionally substituted naphthol, or long chain alkanol, with a higherboiling point than any other alkyl alcohol or aromatic hydroxy compound present or formed in the reaction medium. In this way there will tend to be formed a titanate ester or a mixture of titanate esters with a higher boiling point than any other material present. Examples of phenols that can be added include o-, m- and p- alkylphenols, dialkyl phenols, α-naphthol, and mixtures thereof. Specific examples include iso-nonylphenol (prepared by reaction of propylene trimer with phenol in the presence of an alkylation catalyst, and homologues thereof. n-hexadecanol, n-octadecanol and eicosanol are examples of longer chain alkanols that can be used. Preferably there is used a stoichiometric or near stoichiometric amount of such a higher boiling hydroxy compound, based upon the titanium content of the titanate ester precursor.

In conducting the process of the invention the rates of supply of the dialkyl carbonate and of the aromatic hydroxy compound to the primary reaction zone are preferably selected so as to provide therein a dialkyl carbonate: aromatic hydroxy compound molar ratio in the range of from about 5:1 to about 1:5, more preferably in the range of from about 2:1 to about 1:2. Best results are usually obtained when this molar ratio approximates to about 1:1, e.g. from about 1.2:1 to about 0.8:1, in the first reaction zone.

In the primary reaction zone the aromatic hydroxy compound and the dialkyl carbonate undergo reaction to form an amount of the corresponding alkyl aryl carbonate which is limited by the equilibrium constant of the reaction:

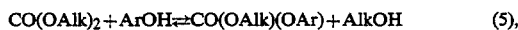

CO(OAlk)₂+ArOH⇌CO(OAlk)(OAr)+AlkOH  (5), where Alk is alkyl, preferably of from 1 to 6 carbon atoms, even more preferably from 1 to 4 carbon atoms, for example methyl, and Ar is a monocyclic aromatic radical, for example phenyl.

The alkyl alcohol formed as co-product in equation (5) is desirably removed from the primary reaction zone, essentially as fast as it is formed, in the overhead vaporous stream recovered therefrom. In this way the formation of the alkyl aryl carbonate is favoured. In addition further reaction may occur to form the corresponding diaryl carbonate:

CO(OAlk)(OAr)+ArOH⇌CO(OAr)₂+AlkOH  (6).

Again, alkyl alcohol (AlkOH) produced by reaction (6) is desirably recovered in the overhead product from the primary reaction zone substantially as fast as it is formed. In this way the formation of diaryl carbonate is favoured.

Besides a minor proportion of alkyl alcohol produced as co-product in equations (5) and (6), the overhead vaporous stream from the primary reaction zone normally contains a much larger proportion each of the aromatic hydroxy compound and of the dialkyl carbonate, as well as some alkyl aryl carbonate. This vaporous overhead stream can be condensed and then separated in two or more stages in an alkyl alcohol recovery zone to be described further below.

The liquid stream recovered from the primary reaction zone contains a minor proportion of aryl alkyl carbonate in admixture with a small amount of diaryl carbonate and with a much larger proportion each of aromatic hydroxy compound and of dialkyl carbonate. In addition it contains transesterification catalyst. This liquid stream is typically passed forward without further treatment to the secondary reaction zone.

When reacting dimethyl carbonate and phenol, the vaporous stream from the primary reaction zone typically exhibits an aromatic hydroxy compound:dialkyl carbonate molar ratio of at least about 0.25:1 up to about 0.75:1, whilst the corresponding alkyl aryl carbonate:dialkyl carbonate molar ratio may range from about 0.001:1 up to about 0.02:1.

When reacting together dimethyl carbonate and phenol the liquid stream from the primary reaction zone typically has an aromatic hydroxy compound:dialkyl carbonate molar ratio which ranges from about 2:1 to about 3:1, whilst the alkyl aryl carbonate:dialkyl carbonate molar ratio may typically lie in the range of from about 0.1:1 to about 0.25:1. It may further contain a minor amount of diaryl carbonate corresponding typically to a diaryl carbonate:dialkyl carbonate molar ratio of from about 0.001:1 to about 0.06:1. Alkyl alcohol may also be present in this liquid stream in an amount corresponding to an alkyl alcohol:dialkyl carbonate molar ratio of from about 0.01:1 to about 0.05:1. It also contains transesterification catalyst.

In the secondary reaction zone further reaction occurs between aromatic hydroxy compound and dialkyl carbonate, since the concentration of alkyl alcohol in the reaction medium is lower than in the reaction medium of the primary reaction zone and alkyl alcohol is being removed in the vapour stream.

Further transesterification catalyst may be added to the secondary reaction zone. However this will not normally be necessary since the liquid stream from the primary reaction zone already contains transesterification catalyst.

An overhead vaporous stream is recovered from the secondary reaction zone which contains a minor amount each of alkyl alcohol, alkyl aryl carbonate, and diaryl carbonate besides a major amount of aromatic hydroxy compound and a lesser amount of dialkyl carbonate. When the dialkyl carbonate is dimethyl carbonate and the aromatic hydroxy compound is phenol the alkyl alcohol:dialkyl carbonate molar ratio in this overhead stream is typically from about 0.02:1 to about 0.2:1, whilst the alkyl aryl carbonate:dialkyl carbonate molar ratio is from about 0.05:1 to about 0.3:1, the aromatic hydroxy compound:dialkyl carbonate molar ratio is from about 1:1 to about 3:1, and the diaryl carbonate:dialkyl carbonate molar ratio is from about 0.0005:1 to about 0.05:1.

In the case when the reactants are dimethyl carbonate and phenol the liquid stream from the secondary reaction zone has an aromatic hydroxy compound:dialkyl carbonate molar ratio which typically ranges from about 5:1 to about 10:1, whilst the alkyl aryl carbonate:-dialkyl carbonate molar ratio may typically lie in the range of from about 0.5:1 to about 2:1. It may further contain a minor amount of diaryl carbonate corresponding typically to a diaryl carbonate:dialkyl carbonate molar ratio of from about 0.005:1 to about 1.25:1. A trace of alkyl alcohol may also be present in this stream in an amount corresponding to an alkyl alcohol:dialkyl carbonate molar ratio of from about 0.005:1 to about 0.05:1. It also contains transesterification catalyst.

The vaporous stream from the secondary reaction zone can be combined with that from the primary reaction zone and the mixed stream passed forward, essentially still at the transesterification pressure, to the alkyl alcohol recovery zone mentioned above. This recovery zone can comprise two distillation columns, the first of which is operated substantially at the transesterification pressure while the second distillation column is operated at a lower pressure. The incoming vaporous stream is condensed in a heat exchanger and the resulting condensate and any vapours remaining uncondensed are passed to the first distillation column. A mixture of alkyl alcohol and dialkyl carbonate is recovered overhead from the first distillation column of the alkyl alcohol recovery zone. This mixture is an azeotropic mixture of methanol and dimethyl carbonate when dimethyl carbonate is used as the dialkyl carbonate. Such a mixture can be recycled for production of further dialkyl carbonate. Also recovered from the first distillation column of the alkyl alcohol recovery zone is a liquid bottom product containing alkyl aryl carbonate, aromatic hydroxy compound, and dialkyl carbonate which is passed through a pressure let down valve to the second distillation column of the alkyl alcohol recovery zone. A mixture containing aromatic hydroxy compound and dialkyl carbonate is recovered overhead from this second distillation column and a much smaller quantity of liquid bottom product is drawn off from the bottom of the column containing a small amount of diaryl carbonate in admixture with alkyl aryl carbonate and aromatic hydroxy compound. The mixture recovered overhead from the second distillation column can be recycled for further reaction, conveniently to the primary reaction zone, while the corresponding liquid bottom product can be recycled to the tertiary reaction zone.

Since the second distillation column of the alkyl alcohol recovery zone is operated at a lower pressure than the first distillation column thereof, it is feasible to utilise the heat exchanger that condenses the vaporous stream or streams from the primary and/or secondary reaction zones as the column reboiler for the second distillation column of the alkyl alcohol recovery zone. In this way the heat of vaporisation of the vaporous stream or streams is utilised to good advantage and the overall efficiency of the plant is enhanced.

The liquid bottom product from the second distillation column of the alkyl alcohol recovery zone can be admixed with the liquid bottom stream from the secondary reaction zone prior to admission to the tertiary reaction zone. Since the resulting liquid mixture is essentially free from alkyl alcohol and since the conditions in the primary and secondary reaction zones are advantageously selected so as to maximise the content of alkyl aryl carbonate in the feed to the tertiary reaction zone, this means that the conversion of alkyl aryl carbonate to diaryl carbonate according to equation (6) above can be maximised in the tertiary reaction zone.

From the tertiary reaction zone there is recovered overhead a vaporous overhead stream containing a trace of alkyl alcohol, besides a major amount of aromatic hydroxy compound and a lesser amount of dialkyl carbonate. When using dimethyl carbonate as the dialkyl carbonate and phenol as the aromatic hydroxy compound the alkyl alcohol:dialkyl carbonate molar ratio in the vaporous stream is typically from about 0.001:1 to about 0.05:1 whilst the aromatic hydroxy compound:dialkyl carbonate molar ratio is typically from about 3:1 to about 8:1.

The liquid bottom stream from the tertiary reaction zone contains a trace of alkyl alcohol, besides alkyl aryl carbonate, aromatic hydroxy compound, dialkyl carbonate and diaryl carbonate. Typical ranges of molar ratios when using dimethyl carbonate as the dialkyl carbonate and phenol as the aromatic hydroxy compound are as follows: alkyl alcohol:dialkyl carbonate about 0.001:1 to about 0.1:1; alkyl aryl carbonate:dialkyl carbonate about 6:1 to about 30:1; aromatic hydroxy compound:dialkyl carbonate about 15:1 to about 40:1; and diaryl carbonate:dialkyl carbonate about 5:1 to about 20:1.

The vaporous product from the tertiary reaction zone can be condensed and passed to the alkyl alcohol recovery zone, whilst the liquid product stream from the tertiary reaction zone is passed on to a diaryl carbonate recovery zone in which diaryl carbonate is recovered therefrom in a product recovery zone which may comprise one or more distillation columns in series operated under normal pressure, or preferably under vacuum, e.g. a vacuum of from about 0.001 bar up to about 0.95 bar.

In the product recovery zone there may also be recovered unreacted starting materials, i.e. dialkyl carbonate and aromatic hydroxy compound, as well as intermediate product, i.e. alkyl aryl carbonate. These can be recycled to the process, conveniently to the tertiary reaction zone. In the product recovery zone a stream or streams containing by-products, such as diaryl ether and alkyl aryl ether, may be produced. The levels of such by-products can be controlled by withdrawing appropriate purge streams.

The aromatic hydroxy compound may be an optionally substituted monocyclic aromatic hydroxy compound. As examples of suitable aromatic compounds there can be mentioned 2-, 3- or 4-methoxy-, -ethoxy-, or -n-butoxy-phenol, o-, m- or p- cresol, guiaicol, 2,3-dimethoxyphenol, 2,3-, 2,4-, 2,5-, 2,6-, or 3,4-dimethylphenol, 2-, 3-, or 4- ethylphenol, 2-, 3- or 4-n-propylphenol, 2-, 3- or 4-iso-propylphenol, 2,4- or 2,6-diethylphenol, and the like. Of especial interest is phenol itself.

The dialkyl carbonate used as starting material is preferably derived from an alkanol containing from 1 to about 6 carbon atoms. Such alkanols include ethanol, N-propanol, iso-propanol, n-butanol, iso-butanol, n-pentanol, iso-pentanol, and n-hexanol. Methanol is an especially preferred alkanol from which the dialkyl carbonate is derived. Hence a preferred dialkyl carbonate is dimethyl carbonate. However, there can also be mentioned diethyl carbonate, di-n-propyl carbonate, di-iso-propyl carbonate, di-n-butyl carbonate, di-iso-butyl carbonate, di-n-pentyl carbonate, di-iso-pentyl carbonate, di-n-hexyl carbonate, and the like.

BRIEF DESCRIPTION OF THE DRAWINGS

In order that the invention may be clearly understood and readily carried into effect, a preferred process for the production of diphenyl carbonate according to the teachings of the present invention will now be described, by way of example only, with reference to the accompanying drawings, wherein.

Figure 1:
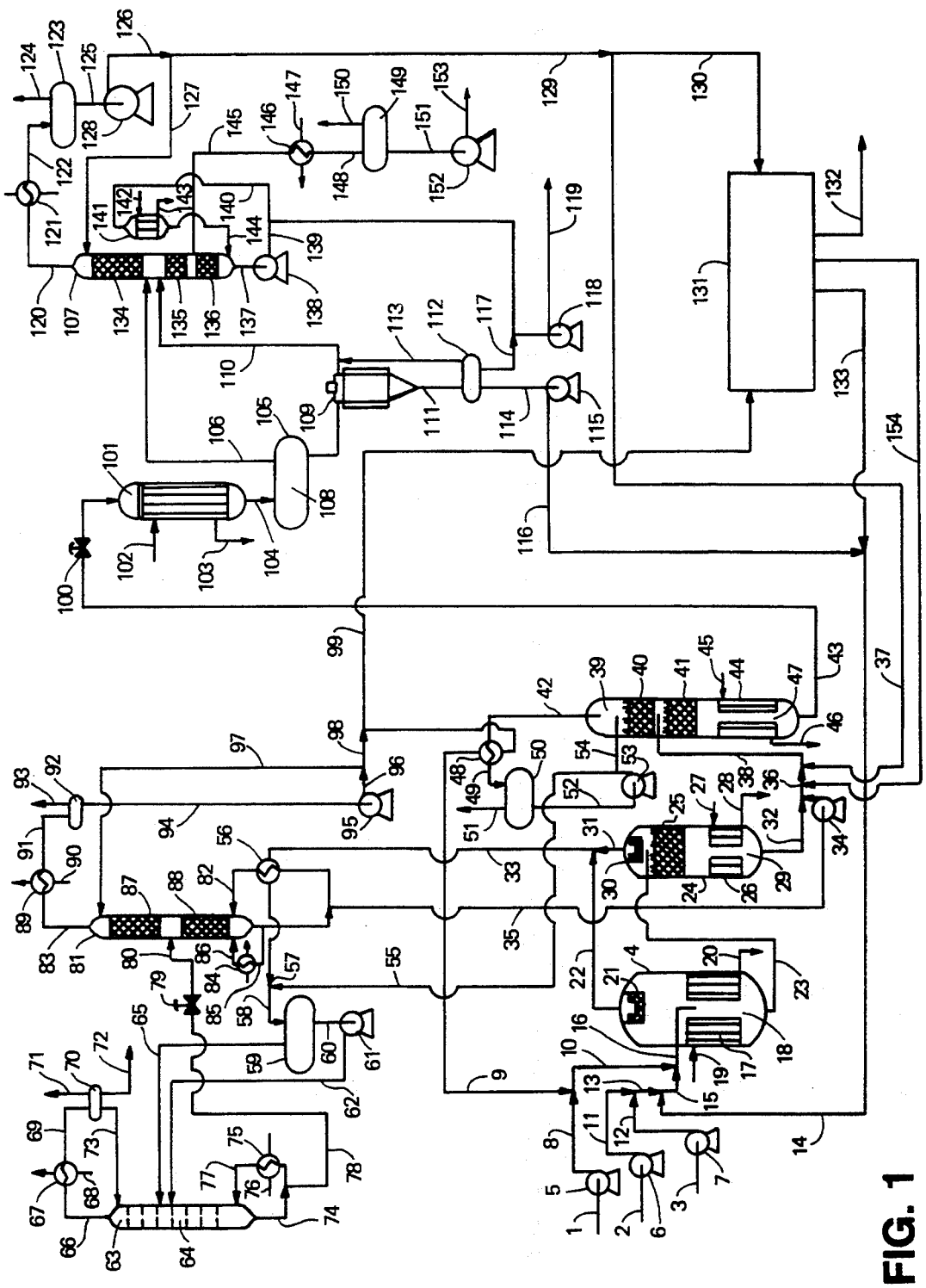
FIG. 1 is a flow sheet of a plant for the production of diphenyl carbonate utilising the process of the invention.

It will be understood by those skilled in the art that, as the drawings are diagrammatic, further items of equipment may be required additionally in a commercial plant, such as temperature sensors, pressure sensors, pressure relief valves, control valves, level controllers, and the like. The provision of such ancillary items of equipment forms no part of the present invention and will be in accordance with conventional chemical engineering practice. Moreover it is not intended that the scope of the invention should be limited in any way by the precise methods used for heating and cooling the various process streams, or by the arrangement of coolers, heaters, and heat exchangers shown in the drawings. Any other suitable arrangement of equipment fulfilling the requirements of the invention may be used in place of the illustrated equipment in accordance with normal chemical engineering techniques.

Referring to FIG. 1 of the drawings, there is illustrated a plant for the production of diphenyl carbonate from phenol and dimethyl carbonate by reaction in the presence of a transesterification catalyst, such as a titanium tetra-alkoxide. An example of a suitable transesterification catalyst precursor is the material sold as "Tilcom BIP" by Tioxide U.K. Limited of Tioxide House, 137-143 Hammersmith Road, London W14 0QL. (The word "Tilcom" is a Registered Trade Mark). This material is described by its manufacturers as a modified form of tetra-iso-propyl titanate in which approximately 13% of the iso-propoxy groups have been replaced by n-butoxy groups. It is a pale yellow liquid (pour point −30° C., boiling point 236° C.).

Make-up transesterification catalyst precursor is supplied to the plant in line 1, whilst phenol and dimethyl carbonate are fed to the plant in lines 2 and 3 respectively. The reagents and catalyst precursor are pumped into primary reactor 4 by means of pumps 5, 6 and 7 respectively. The make-up catalyst flows from pump 5 in line 8 and is admixed with a recycled mixture of phenol and dimethyl carbonate in line 9; the resulting mixture is passed on towards primary reactor 4 in line 10. Phenol is pumped by pump 6 through line 11, and is mixed with dimethyl carbonate, which is pumped forward by pump 7 in line 12, to form a mixed stream in line 13. This is admixed with recycled reactants in line 14 and the mixture flows on in line 15 to meet the recycle stream in line 10 so as to form the feed mixture to primary reactor 4 in line 16.

Primary reactor 4 is equipped with an internal heat exchanger 17 having a vertical axial passage 18 for descending liquid, the horizontal cross sectional area of passage 18 being approximately equal to the corresponding horizontal cross sectional area of the vertical tubes contained in heat exchanger 17.

Heat exchanger 17 is also equipped with a steam supply line 19 and a condensate drain line 20, as well as a vent line (not shown) in the upper part of the steam side of heat exchanger 17 through which permanent gases, such as air, that would otherwise accumulate in the steam space and hinder heat transfer, can be discharged. Primary reactor 4 is also fitted with a mist coalescer 21, with an overhead line 22 for vapour exit and with a bottom line 23 for liquid egress. The pressure in primary reactor 4 is typically in the region of 5 bar and the temperature is typically about 220° C. The rates of supply of dimethyl carbonate, of phenol, and of the catalyst are usually chosen so as to provide in primary reactor 4 an approximately 50:50 molar mixture of dimethyl carbonate and phenol and a Ti concentration of between about 15 ppm and about 35 ppm, measured on a wt./vol. basis.

It will be appreciated that, although the transesterification catalyst is charged to the primary reactor 4 in the form of a mixture of tetra-alkoxy titanates, the alkoxy groups can undergo exchange reactions with other groups such as phenoxy groups. Hence at least a proportion, it is believed, of the titanium will be present in the reaction mixture in primary reactor 4 as tetraphenyl titanate in admixture with mixed alkyl/aryl titanates containing 1, 2, or 3 phenoxy groups.

A relatively methanol-rich vapour is recovered overhead from primary reactor 4 in line 22 and a relatively methanol-poor liquid leaves primary reactor 4 via line 23. The compositions of these streams approach the chemical and vapour-liquid equilibrium values under the temperature and pressure conditions prevailing in primary reactor 4.

In operation of primary reactor 4 a mixture of liquid and vapour rises through the vertical tubes of heat exchanger 17, the vapour disengages in the head space of primary reactor 4 and liquid descends through the axial passage 18. The resulting vigorous circulation induced by the boiling liquid establishes good mixing of the contents of primary reactor 4 and obviates any requirement for mechanical agitation.

Liquid in line 23 is passed to the top of a secondary reactor 24 and is distributed over the top of structured packing 25. Secondary reactor 24 is fitted with a heat exchanger 26, which is supplied with steam in line 27 and has a condensate drain 28; secondary reactor 24 also has a vertical axial passage 29, a mist condenser 30, a vapour exit line 31, and a liquid exit line 32. Countercurrent contact of vapours and liquid (which contains titanium-containing transesterification catalyst) over packing 25 enhances the removal of methanol in the vapour stream in line 31. The contents of the lower part of secondary reactor 24 are thermally mixed by heat exchanger 26 in a similar manner to that described above in relation to primary reactor 4.

The vapour streams in lines 22 and 31 are combined to form a stream in line 33 which is passed to a methanol recovery section which is described further below.

The liquid leaving secondary reactor 24 in line 32 contains methyl phenyl carbonate. It is mixed with a methyl phenyl carbonate concentrate stream recycled from the above-mentioned methanol recovery section by pump 34 in line 35. The resulting mixed stream in line 36 is further mixed with a recycle stream containing methyl phenyl carbonate in line 37 from a diphenyl carbonate recovery section which will be described further below. The combined methyl phenyl carbonate concentrate stream passes on in line 38 to provide a feed stream to a tertiary reactor 39.

Tertiary reactor 39 is equipped with two beds of structured packing 40 and 41. The feed stream from line 38 is distributed over the top of the lower bed 41. The reactor 39 is also fitted with vapour and liquid exit lines 42 and 43 respectively, as well as with a heat exchanger 44 which is supplied with steam in line 45 and drained of condensate by line 46. There is an axial passage 47 in tertiary reactor 39, by means of which thermally driven mixing can be achieved in tertiary reactor 39 in a similar manner to that achieved in primary reactor 4 and in secondary reactor 24.

The vapours from reactor 39 in line 42 are condensed against a stream of recycled reactants in line 9 by passage through condenser 48 and pass via line 49 to a reflux drum 50. This is vented by line 51 and a pressure control valve (not shown). Liquid passes via line 52 and reflux pump 53 through line 54 to the top of bed 40; reflux of liquid through bed 40 reduces the loss of methyl phenyl carbonate from the top of tertiary reactor 39 to very small amounts.

Pump 53 also delivers liquid from reflux drum 50 via line 55 to the methanol recovery section (yet to be described). This liquid contains a mixture of phenol and diphenyl carbonate with a minor amount of methanol.

The liquid in line 43 passes forward to a product recovery section, which is described further below, in which diphenyl carbonate is recovered therefrom.

The vapours from primary reactor 4 and secondary reactor 24 combine from lines 22 and 31 in line 33 and are condensed in passage through a heat exchanger 56. The nearly totally condensed vapours pass along line 57 and are admixed with liquid in line 55 to flow on in line 58 to a drum 59. This mixed feed in line 58 forms the feed to the methanol recovery section to which mention has been made above.

Liquid from drum 59 passes via line 60, pump 61 and line 62 to an intermediate tray of a distillation column 63 which is provided with a multiplicity of distillation trays 64 of conventional design. Any vapours from drum 59 are also conveyed to distillation column 63 in line 65. This distillation column 63 forms the first column of the afore-mentioned methanol recovery section.

A methanol-rich azeotrope containing methanol and dimethyl carbonate is withdrawn from the top of distillation column 63 via line 66 and condenser 67 which is provided with cooling water in line 68. Condensate passes on in line 69 to a drum 70, which is vented by line 71, and is drawn off from the plant in line 72. Reflux to distillation column 63 is provided by gravity feed in line 73; if desired, this reflux stream could be pumped by a pump (not shown) fitted in line 73.

Distillation column 63 is provided with a conventional thermosiphon reboiler assembly, which comprises line 74, heat exchanger 75, with its steam supply line 76, and line 77. A substantially methanol-free liquid is withdrawn in line 78 and is passed through a pressure reduction valve 79 and line 80 to a further distillation column 81 which forms the second distillation column of the methanol recovery section.

Because distillation column 81 operates at a significantly lower pressure than the pressure of the vapours in line 33, heat exchanger 56 can condense these vapours against the boiling liquid in line 82. Thus the heat used in producing vapours in primary reactor 4 and secondary reactor 24 can be used to provide most of the heat required to cause the separation of the overhead products in line 83, which comprise a mixture of phenol and diphenyl carbonate, from the liquid bottom product material in line 84, which is a methyl phenyl carbonate concentrate. Additional heat, as well as start-up heat, for distillation column 81 can be provided by an auxiliary reboiler system comprising steam heated exchanger 84 and lines 85 and 86 at the base of distillation column 81.

Distillation column 81 is provided with two beds of structured packing 87 and 88. Although conventional distillation trays can be used to effect the separation, structured packing is preferred in order to give rise to the minimum pressure drop across distillation column 81.

The overheads recovery system of distillation column 81 is of conventional design; it comprises line 83, condenser 89 with its cooling water supply line 90, line 91, and reflux drum 92, which is vented to a vacuum system (not shown) by means of a pressure control valve (also not shown) and line 93. Condensate from reflux drum 92 is taken in line 94 by reflux pump 95 on into line 96. A part is returned as a reflux stream to distillation column 81 in line 97, whilst the remainder flows on in line 98. The major part of this liquid stream in line 98, which comprises a substantially methanol-free stream of dimethyl carbonate and phenol, is returned to primary reactor 4 in line 9, whilst a minor part is taken in line 99 for a purpose which will be explained further below.

The solution in line 43 comprises diphenyl carbonate, but contains also some dimethyl carbonate, phenol, methyl phenyl carbonate, catalyst, minor amounts of by-products, and traces of methanol. This solution flows through a pressure reducing valve 100 into an evaporator 101. As shown in FIG. 1 evaporator 101 is depicted as being of the falling film type and is supplied with steam in line 102. Water formed by condensation of such steam is drained away in line 103. The major part of the liquid in line 43 is vaporised in passage through falling film evaporator 101 under reduced pressure. The resulting two phase fluid mixture passes down line 104 to separation drum 105. The vapour portion passes via line 106 to product column 107; the liquid portion flows down through line 108 to a further evaporation stage 109, which is depicted in FIG. 1 as being of the wiped film type. Further vapours pass in line 110 to product recovery column 107, whilst the residual liquid fraction from evaporator 109 passes by line 111 to a catalyst residue drum 112 which is vented by line 113 to line 110. Catalyst can be recycled to the primary reactor 4 by line 114, pump 115, line 116, and line 14, or sent to disposal via line 117, pump 118, and line 119.

Product recovery column 101 is provided with a conventional overhead recovery system comprising line 120, condenser 121, line 122, and drum 123, which is vented to a vacuum system (not shown) Via a pressure reduction valve (also not shown) in line 124. Condensate from drum 123 can be recycled to the top of product recovery column 107 via lines 125, 126 and 127 with the aid of pump 128. The net overhead product, which is rich in methyl phenyl carbonate, leaves in line 129. A major portion is recycled to tertiary reactor 39 in line 37 and a minor portion passes via line 130 to a by-product separation stage, which is depicted generally at 131, in which any traces of diphenyl ether and/or anisole that may have been formed are separated from the valuable reactants and intermediates and are sent to disposal in line 132.

By-product separation stage 131 can be of conventional design as any known batch or continuous separation technique can be used to separate the byproducts from the other materials present in the streams in lines 99 and 130. The stream in line 99 is mainly phenol and dimethyl carbonate with a minor amount of anisole, whilst that in line 130 is mainly methyl phenyl carbonate and phenol with minor amounts of anisole and diphenyl ether. The valuable materials from line 99 remaining after removal of anisole are recycled to primary reactor 4 by way of lines 133 and 14. The boiling point data useful in the design of by-product separation stage 131, i.e. the data for the most important potential by-products and for the intermediates and starting materials, are as follows:

| Material | Boiling point (°C. at 760 mm Hg) |
|---|---|
| dimethyl carbonate | 90.3 |
| anisole | 153.7 |
| phenol | 181.9 |
| methyl phenyl carbonate | 152.2 |
| diphenyl ether | 259.0 |
| diphenyl carbonate | 302.0 | structured packing 134, 135, and 136. The vapours in lines 106 and 110 are introduced below bed 134 and a vapour product stream is withdrawn from above bed 134 in line 120, as already described. A liquid containing heavy by-products and some diphenyl carbonate accumulates in the base of column 107. Reboil is provided by equipment comprising line 137, pump 138, lines 139 and 140 and falling film reboiler 141. Reboiler 141 is provided with steam supplied through line 142, whilst condensate drains away in line 143. The two phase fluid is returned to the base of distillation column by means of line 144.

Diphenyl carbonate vapour is taken from column 107 in line 145, between beds 135 and 136, and is condensed in condenser 146 which is provided with tempered water at a temperature above the melting point of diphenyl carbonate (80° C.) in line 147. The resulting molten diphenyl carbonate flows via line 148 to drum 149; this is vented to vacuum by line 150 and a suitable control valve (not shown). Molten diphenyl carbonate then flows on in line 151 and is pumped to a pressure above atmospheric pressure by pump 152 into line 153 in which it exits the plant.

A line 154 connects by-product separation stage 131 and line 36 for recycle of the valuable materials from line 130 that remain after removal of diphenyl ether therefrom.

The compositions of some of the more important streams and the corresponding flow rates in kg moles/hr the plant of FIG. 1 are set out below in Table 1, in which the abbreviations have the following meanings:

MPC=methyl phenyl carbonate;
DMC=dimethyl carbonate; and
DPC=diphenyl carbonate.

TABLE 1

| Line No. | 2 | 3 | 9 | 16 | 22 | 23 | 31 | 32 | 35 | 37 | 43 |
|---|---|---|---|---|---|---|---|---|---|---|---|
| MeOH | — | — | — | — | 42.55 | 6.22 | 9.99 | 0.29 | — | 0.02 | 0.02 |
| MPC | — | — | — | — | 7.56 | 38.55 | 17.97 | 20.65 | 25.53 | 73.45 | 73.45 |
| PhOH | — | 53.48 | 740.24 | 804.36 | 250.63 | 504.96 | 343.08 | 157.82 | 77.40 | 48.30 | 48.30 |
| DMC | 32.18 | — | 763.48 | 804.39 | 533.19 | 223.63 | 199.35 | 22.16 | — | 2.16 | 2.17 |
| DPC | — | — | — | — | 0.02 | 1.14 | 0.26 | 2.71 | 0.28 | — | 26.11 |
| PhOMe | — | — | 52.35 | 52.35 | 22.98 | 29.61 | 22.97 | 6.77 | — | 0.88 | 0.88 |
| PhOPh | — | — | — | — | trace | 0.05 | 0.04 | 0.11 | 0.04 | 19.99 | 20.24 |
| CO$_2$ | — | — | — | — | 0.28 | 0.02 | 0.25 | trace | — | trace | trace |

| Line No. | 55 | 72 | 78 | 98 | 99 | 129 | 130 | 132 | 133 | 153 | 154 |
|---|---|---|---|---|---|---|---|---|---|---|---|
| MeOH | 0.94 | 53.48 | Trace | — | — | 0.02 | trace | — | — | — | trace |
| MPC | — | — | 25.53 | — | — | 73.48 | 0.91 | — | — | — | 0.91 |
| PhOH | 234.57 | — | 828.29 | 750.88 | 10.65 | 48.30 | 0.60 | — | 10.65 | — | 0.60 |
| DMC | 44.73 | 2.81 | 774.46 | 774.46 | 10.98 | 2.17 | 0.03 | 2.26 | 6.46 | — | 0.03 |
| DPC | — | — | 0.28 | — | — | — | — | — | — | 26.11 | — |
| PhOMe | 7.14 | — | 53.10 | 53.10 | 0.75 | 0.88 | 0.01 | 0.75 | — | — | 0.01 |
| PhOPh | — | — | 0.04 | — | — | 20.24 | 0.25 | 0.25 | — | — | — |
| CO$_2$ | 0.48 | 1.00 | — | — | — | trace | trace | — | — | — | trace |

Figure 2:
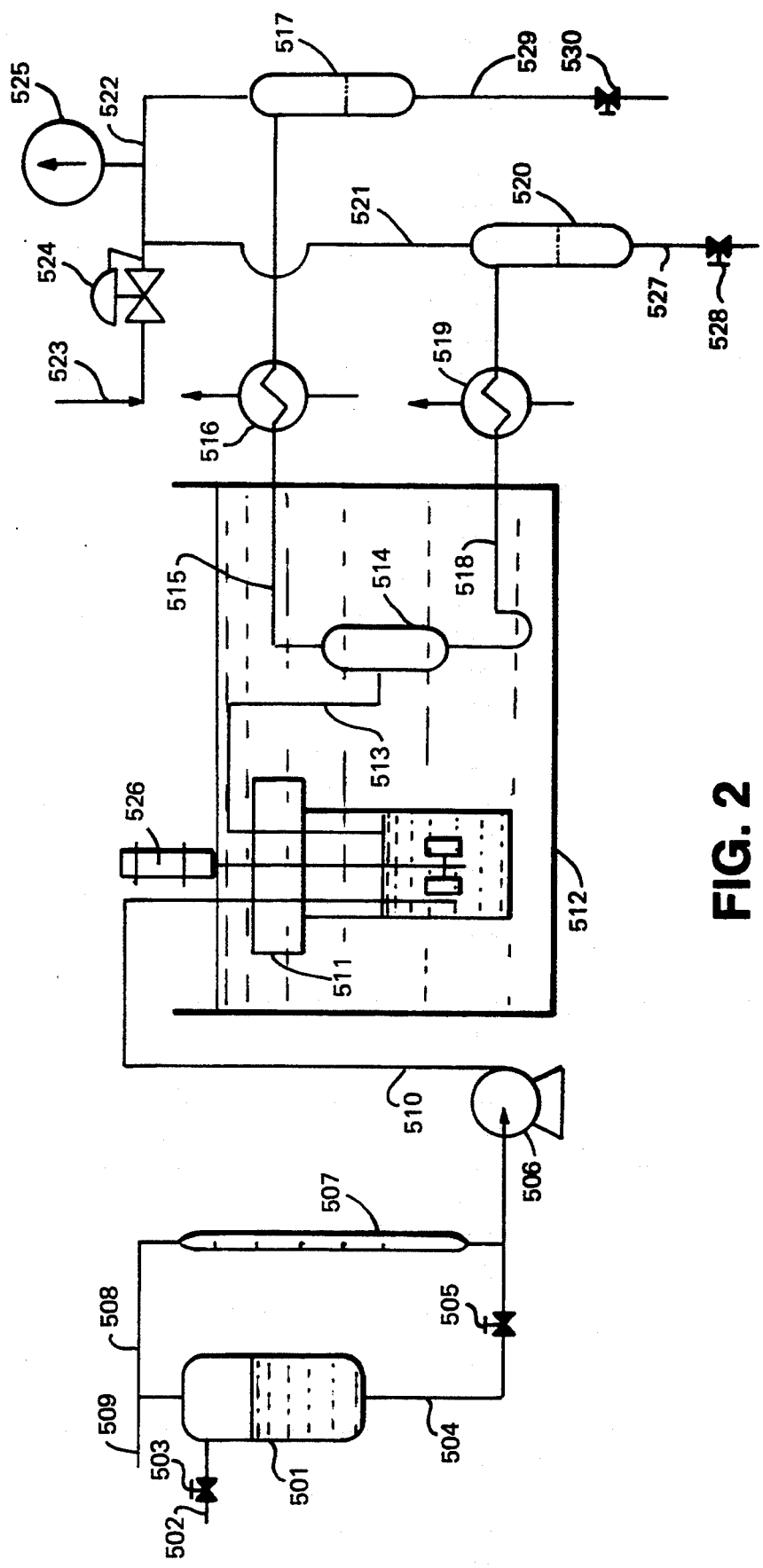
FIG. 2 is a diagram of an experimental apparatus used in the Examples.

An experimental apparatus used in the Examples set out below is illustrated in FIG. 2 of the accompanying drawings.

In FIG. 2 a feed supply vessel 501 can be charged with liquid through line 502 from an external supply under the control of valve 503. This feed liquid flows in line 504 through valve 505 to pump 506. Glass burette 507 can be used to check the delivery rate of pump 506 when valve 505 is closed. Line 508 connects the vapour spaces of vessel 501 and burette 507 and is itself connected to a supply line 509 for dry O$_2$-free nitrogen at just above atmospheric pressure. With the exception of the feed vessel and the check burette, which are made from borosilicate glass, all other components with which the liquid comes into contact are made from "Stainless Steel 316".

Pump 506 delivers the feed liquid through line 510 to reaction vessel 511 which is immersed in a thermostatically controlled oil-filled heating bath 512 which is heated electrically besides being mechanically agitated. Liquid enters reaction vessel 511 at the end of line 510 below the level of the surface of the heated oil. A mixture of liquid and vapour leaves reaction vessel 511 via line 513 and enters separation vessel 514. In vessel 514 the vapour and liquid separate, the vapour proceeding by line 515, which passes through the wall of the heating bath 512, and being condensed in condenser 516.

The resulting condensate collects in vessel 517. In order to avoid any possibility of condensate running back into separation vessel 514 line 515 slopes downwardly towards vessel 517. The liquid collecting in separation vessel 514 proceeds via line 518 through the wall of heating bath 512 to cooler 519 and is collected in vessel 520. The vapour spaces of vessels 517 and 520 are connected via lines 521 and 522. Line 523 is connected to a high pressure nitrogen supply. Pressure control valve 524 is used to maintain a preselected pressure in lines 521 and 522; this pressure is monitored by gauge 525 and constitutes the operating pressure for all equipment downstream from the pump 506. Precision thermocouples (not shown) are located in the liquid phase in reactor 511, in line 513 and in vessel 514. Reference numeral 526 indicates a stirrer for reactor 511. Product liquid can be sampled from vessel 520 using line 527 and valve 528, while condensate from vessel 517 can be drawn off through line 529 using valve 530.

The empty system is purged with nitrogen using lines 502 and 523 as feed points and line 527 and 529 as vents. The feed vessel is then loaded with the chosen liquid mixture through line 502. Valve 505 is opened and pump 506 is then started. When liquid has accumulated in reactor 511 such that it is flowing through line 513 into vessel 514, and through line 518 to vessel 520, such that liquid emerges from line 527 with valve 528 open, the desired flow rate of liquid is established and then the pressure and temperature are adjusted to the desired values. Vessels 517 and 520 are carefully drained and then a run is started. After a known period of time the liquid contents of vessels 517 and 520 are collected and analysed. From the resulting data, i.e. the feed liquid composition, and the masses and compositions of the liquid materials collected from vessels 517 and 520, it is possible to calculate the vapour and liquid composition of the stream in line 513, and hence the extent of the reaction and the vapour/liquid partition data, under controlled conditions of temperature, pressure and residence time. Analysis of the liquid samples is effected using gas/liquid chromatography using a Pye Unicam gas/liquid chromatograph with an OV151 capillary column 25 meters long at an inlet pressure of 2.74 bar, using helium as carrier gas and a flame ionisation detector, The temperature of the column is held for 1 minute at 100° C. after injection and then raised at 20° C./minute to 280° C. and then held at 280° C., Under these conditions the compounds exhibit the following retention times:

| Compound | Retention time (minutes) |
| --- | --- |
| Methanol | 1.31 |
| Dimethyl carbonate | 1.43 |
| Anisole | 2.38 |
| Phenol | 2.87 |
| Methyl phenyl carbonate | 5.13 |
| Diphenyl ether | 6.6 |
| Diphenyl carbonate | 10.25 |

The catalyst precursor used was tetraphenyl titanate. This was prepared by charging 10.11 g of diphenyl carbonate, 25.40 g of phenol, and 9.87 g of iso-propyl n-butyl titanate (Tilcom BIP) to a spinning band still and refluxing the resulting solution for 1 h. Subsequently iso-propanol, n-butanol and eventually excess phenol were allowed to distil overhead, leaving 15.77 g of a tetraphenyl titanate/diphenyl carbonate concentrate which was homogeneous and liquid at 200° C. On cooling to room temperature the solution solidified. In the course of this procedure the catalyst concentrate was exposed to a temperature of 300° C. for 1 h. A 50/50 molar mixture of dimethyl carbonate and phenol was prepared and sufficient of the catalyst concentrate was dissolved therein to obtain a feed solution with a titanium concentration of 33 ppm w/v.

The invention is further illustrated in the following Examples. In Example 1 tetraphenyl titanate was used as catalyst whilst Examples 2 to 11 used "Tilcom BIP" catalyst. Examples 1 to 6 exemplify conditions appropriate for use in the primary reactor of the process of the invention. Examples 7 to 10 exemplify conditions for the secondary reactor and Example 11 those for the lower part of the tertiary reactor.

The abbreviations used in the Examples have the following meanings:
DMC=dimethyl carbonate;
MPC=methyl phenyl carbonate;
DPC=diphenyl carbonate; and
w/v=weight by volume.

EXAMPLE 1

The conditions were as follows:

| Feed rate (ml/h) | 401.8 |
| --- | --- |
| Feed composition (mol % DMC/PhOH) | 50/50 |
| Catalyst concentration (ppm Ti w/v) | 33 |
| Pressure in psia (bar) | 75 (5.17) |
| Temperature °C. | 218 |
| Test period (minutes) | 30 |
| Moles DMC in | 1.1660 |
| Moles PhOH in | 1.1659 |

The results obtained are summarised below:

| | Liquid product | Vapour product |
| --- | --- | --- |
| Weight (g) | 89.19 | 124.45 |
| Volume (ml) | 84.00 | 119.50 |
| Gram moles | 0.9258 | 1.3953 |

| | Mol % liquid | Mol % vapour |
| --- | --- | --- |
| MeOH | 0.662 | 4.883 |
| DMC | 23.360 | 60.268 |
| PhOH | 67.973 | 33.766 |
| MPC | 5.682 | 1.078 |
| DPC | 0.322 | 0.00498 |
| Anisole | 0.008 | 0.0093 |

EXAMPLE 2

The conditions were as follows:

| Feed rate (ml/h) | 401.7 |
| --- | --- |
| Feed composition (mol % DMC/PhOH) | 50/50 |
| Catalyst concentration (ppm Ti w/v) | 33 |
| Pressure in psia (bar) | 75 (5.17) |
| Temperature °C. | 218 |
| Test period (minutes) | 30 |
| Moles DMC in | 1.1649 |
| Moles PhOH in | 1.1647 |

The results obtained are summarised below:

| | Liquid product | Vapour product |
| --- | --- | --- |
| Weight (g) | 87.74 | 123.76 |
| Volume (ml) | 84.00 | 117.50 |
| Gram moles | 0.9135 | 1.3876 |

| | Mol % liquid | Mol % vapour |
| --- | --- | --- |
| MeOH | 0.751 | 4.933 |
| DMC | 25.201 | 59.811 |
| PhOH | 68.293 | 34.159 |
| MPC | 5.464 | 1.09 |
| DPC | 0.292 | 0.0061 |
| Anisole | 0.00725 | 0.00735 |

EXAMPLE 3

The conditions were as follows:

| Feed rate (ml/h) | 198.4 |
| --- | --- |
| Feed composition (mol % DMC/PhOH) | 50/50 |
| Catalyst concentration (ppm Ti w/v) | 33 |
| Pressure in psia (bar) | 75 (5.17) |
| Temperature °C. | 218 |
| Test period (minutes) | 60 |
| Moles DMC in | 1.1544 |
| Moles PhOH in | 1.1487 |

The results obtained are summarised below:

| | Liquid Product | Vapour product |
| --- | --- | --- |
| Weight (g) | 84.75 | 126.35 |
| Volume (ml) | 80.00 | 119.00 |
| Gram moles | 0.8804 | 1.4276 |

| | Mol % liquid | Mol % vapour |
| --- | --- | --- |
| MeOH | 0.864 | 6.14 |
| DMC | 24.46 | 59.67 |
| PhOH | 68.45 | 32.99 |
| MPC | 5.94 | 1.193 |
| DPC | 0.279 | 0.0067 |
| Anisole | 0.0115 | 0.0137 |

EXAMPLE 4

The conditions were as follows:

| Feed rate (ml/h) | 397.7 |
| --- | --- |
| Feed composition (mol % DMC/PhOH) | 50/50 |
| Catalyst concentration (ppm Ti w/v) | 16.5 |
| Pressure in psia (bar) | 75 (5.17) |
| Temperature °C. | 218 |
| Test period (minutes) | 30 |

-continued

| | | |
|---|---|---|
| Moles DMC in | 1.1525 | |
| Moles PhOH in | 1.1519 | |

The conditions were as follows:

| | Liquid product | Vapour product |
|---|---|---|
| Weight (g) | 86.51 | 123.54 |
| Volume (ml) | 81.50 | 117.00 |
| Gram moles | 0.9061 | 1.3978 |
| | Mol % liquid | Mol % vapour |
| MeOH | 0.606 | 3.956 |
| DMC | 24.71 | 62.077 |
| PhOH | 69.978 | 33.156 |
| MPC | 4.401 | 0.808 |
| DPC | 0.245 | 0.0036 |
| Anisole | 0.0097 | 0.0101 |

EXAMPLE 5

The conditions were as follows:

| | |
|---|---|
| Feed rate (ml/h) | 402.5 |
| Feed composition (mol % DMC/PhOH) | 48.5/51.5 |
| Catalyst concentration (ppm Ti w/v) | 33 |
| Pressure in psia (bar) | 87.5 (6.03) |
| Temperature °C. | 226 |
| Test period (minutes) | 30 |
| Moles DMC in | 1.1345 |
| Moles PhOH in | 1.2069 |

The results obtained are summarised below:

| | Liquid product | Vapour product |
|---|---|---|
| Weight (g) | 96.04 | 117.20 |
| Volume (ml) | 90.00 | 112.00 |
| Gram moles | 0.9989 | 1.3171 |
| | Mol % liquid | Mol % vapour |
| MeOH | 0.801 | 5.427 |
| DMC | 25.283 | 58.717 |
| PhOH | 67.944 | 34.66 |
| MPC | 5.672 | 1.187 |
| DPC | 0.299 | 0.008 |
| Anisole | 0.0177 | 0.0193 |

EXAMPLE 6

The conditions were as follows:

| | |
|---|---|
| Feed rate (ml/h) | 596.9 |
| Feed composition (mol % DMC/PhOH) | 50/50 |
| Catalyst concentration (ppm Ti w/v) | 33 |
| Pressure in psia (bar) | 85.5 (5.89) |
| Temperature °C. | 224 |
| Test period (minutes) | 30 |
| Moles DMC in | 1.738 |
| Moles PhOH in | 1.733 |

The results obtained are summarised below:

| | Liquid product | Vapour product |
|---|---|---|
| Weight (g) | 131.37 | 189.88 |
| Volume (ml) | 123.50 | 180.00 |
| Gram moles | 1.3644 | 2.1231 |
| | Mol % liquid | Mol % vapour |
| MeOH | 0.696 | 4.543 |
| DMC | 24.292 | 60.104 |
| PhOH | 69.059 | 34.233 |
| MPC | 5.582 | 1.112 |
| DPC | 0.37 | 0.0077 |
| Anisole | 0.00894 | 0.00934 |

EXAMPLE 7

The feed solution had the following mol % composition:

MeOH 1.080; DMC 26.700; PhOH 66.380; MPC 5.560; DPC 0.277; and anisole 0.017.

The conditions were as follows:

| | |
|---|---|
| Feed rate (ml/h) | 195.2 |
| Pressure in psia (bar) | 40.4 (2.78) |
| Temperature °C. | 216.5 |
| Test period (minutes) | 60 |
| Moles feed in | 2.1863 |

The results obtained are summarised below:

| | Liquid product | Vapour product |
|---|---|---|
| Weight (g) | 49.90 | 162.56 |
| Volume (ml) | 47.00 | 153.00 |
| Gram moles | 0.4803 | 1.7434 |
| | Mol % liquid | Mol % vapour |
| MeOH | 0.157 | 2.847 |
| DMC | 8.942 | 31.32 |
| PhOH | 76.346 | 62.03 |
| MPC | 11.472 | 3.71 |
| DPC | 3.082 | 0.097 |
| Anisole | 0.0246 | 0.04 |

EXAMPLE 8

The feed solution had the following mol % composition:

MeOH 0.780; DMC 24.562; PhOH 68.791; MPC 5.525; DPC 0.342; and anisole 0.010.

The conditions were as follows:

| | |
|---|---|
| Feed rate (ml/h) | 401.9 |
| Pressure in psia (bar) | 60 (4.13) |
| Temperature °C. | 224 |
| Test period (minutes) | 30 |
| Moles feed in | 2.2427 |

The results obtained are summarised below:

| | Liquid product | Vapour product |
|---|---|---|
| Weight (g) | 138.82 | 76.81 |
| Volume (ml) | 130.00 | 74.00 |
| Gram moles | 1.4018 | 0.8453 |
| | Mol % liquid | Mol % vapour |
| MeOH | 0.458 | 4.37 |
| DMC | 13.636 | 42.489 |
| PhOH | 76.687 | 50.993 |
| MPC | 8.39 | 2.125 |
| DPC | 0.829 | 0.0215 |
| Anisole | 0.0245 | 0.0361 |

EXAMPLE 9

The feed solution had the following mol % composition:

MeOH 0.780; DMC 24.562; PhOH 68.791; MPC 5.525; DPC 0.342; and anisole 0.00974.

The conditions were as follows:

| Feed rate (ml/h) | 401.9 |
|---|---|
| Pressure in psia (bar) | 60 (4.13) |
| Temperature °C. | 231.5 |
| Test period (minutes) | 30 |
| Moles feed in | 2.2428 |

The results obtained are summarised below:

|  | Liquid product | Vapour product |
|---|---|---|
| Weight (g) | 86.17 | 129.46 |
| Volume (ml) | 80.50 | 123.00 |
| Gram moles | 0.84787 | 1.3986 |
|  | Mol % liquid | Mol % vapour |
| MeOH | 0.2745 | 3.333 |
| DMC | 10.202 | 32.781 |
| PhOH | 77.406 | 60.608 |
| MPC | 10.217 | 3.212 |
| DPC | 1.902 | 0.066 |
| Anisole | 0.0285 | 0.0439 |

EXAMPLE 10

The feed solution had the following mol % composition:

MeOH 0.781; DMC 25.562; PhOH 68.365; MPC 5.049; DPC 0.244; and anisole 0.012.

The conditions were as follows:

| Feed rate (ml/h) | 401.6 |
|---|---|
| Pressure in psia (bar) | 57.1 (3.93) |
| Temperature °C. | 231.5 |
| Test period (minutes) | 30 |
| Moles feed in | 2.2429 |

The results obtained are summarised below:

|  | Liquid product | Vapour product |
|---|---|---|
| Weight (g) | 58.57 | 157.30 |
| Volume (ml) | 56.40 | 147.80 |
| Gram moles | 0.5669 | 1.6823 |
|  | Mol % liquid | Mol % vapour |
| MeOH | 0.192 | 2.540 |
| DMC | 8.644 | 29.381 |
| PhOH | 77.364 | 64.303 |
| MPC | 10.945 | 3.675 |
| DPC | 2.854 | 0.101 |
| Anisole | 0.023 | 0.0371 |

EXAMPLE 11

The feed solution had the following mol % composition:

MeOH<0.001; DMC 7.857; PhOH 69.574; MPC 19.465; DPC 2.925; and anisole 0.0534.

The conditions were as follows:

| Feed rate (ml/h) | 298.00 |
|---|---|
| Pressure in psia (bar) | 44.5 (3.07) |
| Temperature °C. | 246.5 |
| Test period (minutes) | 45 |
| Moles feed in | 2.2317 |

The results obtained are summarised below:

|  | Liquid product | Vapour product |
|---|---|---|
| Weight (g) | 53.25 | 188.60 |
| Volume (ml) | N/D | N/D |
| Gram moles | 0.396 | 1.8306 |
|  | Mol % liquid | Mol % vapour |
| MeOH | <0.01 | 1.192 |
| DMC | 1.7848 | 10.447 |
| PhOH | 53.3164 | 72.536 |
| MPC | 21.4379 | 14.197 |
| DPC | 23.4521 | 1.628 |
| Anisole | 0.054 | 0.136 |

EXAMPLE 12 to 22

In these Examples the catalyst precursor is titanium tetra-(iso-nonylphenyl) titanate. This is prepared in substantially the same manner as tetraphenyl titanate except that phenol is replaced by iso-nonylphenol. The results obtained are similar to those described for Examples 1 to 11.

EXAMPLES 23 to 55

Dimethyl carbonate is replaced in the procedures of Examples 1 to 11 by an equivalent amount of the following compounds:

| diethyl carbonate | (Examples 23 to 33) |
|---|---|
| di-iso-propyl carbonate | (Examples 34 to 44) |
| di-n-pentyl carbonate | (Examples 45 to 55). |

EXAMPLES 56 to 110

The procedures of Examples 1 to 11 are repeated using, in place of phenol:

| o-cresol | (Examples 56 to 66) |
|---|---|
| guiaicol | (Examples 67 to 77) |
| 2,4-dimethylphenol | (Examples 78 to 88) |
| 4-ethylphenol | (Examples 89 to 99) |
| m-cresol | (Examples 100 to 110) |

Similarly good results are obtained: however, the compositions of the vapour and liquid streams reflect the lower volatility of these aromatic hydroxy compounds.

EXAMPLES 111 to 121

When tetraphenyl titanate is replaced in the procedures of Examples 1 to 11 by lead borate similarly good results are obtained.

What is claimed is:

1. A continuous process for the production of a diaryl carbonate which comprises:
   (a) providing a plurality of reaction zones including a primary reaction zone, a secondary reaction zone, and a tertiary reaction zone;
   (b) supplying to the primary reaction zone a dialkyl carbonate and an aromatic hydroxy compound;
   (c) maintaining the primary reaction zone under reaction conditions conducive to formation of the corresponding alkyl aryl carbonate;
   (d) reacting the dialkyl carbonate and the aromatic hydroxy compound together in the primary reaction zone in the presence of a transesterification catalyst;
   (e) recovering from the primary reaction zone a vaporous stream comprising alkyl alcohol and a liquid stream comprising alkyl aryl carbonate and depleted in alkyl alcohol;

(f) maintaining the secondary reaction zone under reaction conditions conducive to formation of the corresponding alkyl aryl carbonate;

(g) reacting material of the liquid stream of step (e) in the secondary reaction zone with further aromatic hydroxy compound in the presence of a transesterification catalyst to produce further alkyl aryl carbonate;

(h) recovering from the secondary reaction zone a substantially alkanol-free liquid bottom stream containing alkyl aryl carbonate and excess aromatic hydroxy compound and an overhead vaporous stream;

(i) passing material of the bottom stream of step (h) to the tertiary reaction zone;

(j) maintaining the tertiary reaction zone under temperature and pressure conditions conducive to formation of diaryl carbonate; and (k) recovering from the tertiary reaction zone a liquid bottom product containing diaryl carbonate and a vaporous overhead stream comprising aromatic hydroxy compound and dialkyl carbonate.

2. A process according to claim 1, in which the transesterification catalyst is selected from Lewis acids, salts, esters of transition metals, organic and inorganic borates, and mixtures thereof.

3. A process according to claim 1, in which the transesterification catalyst comprises one or more titanate esters selected from tetra alkyl titanates, tetraaryl titanates, mixed alkylaryl titanates, and mixtures thereof.

4. A process according to claim 1, in which the transesterification conditions include a temperature in the range of from about 25° C. to about 350° C., a pressure of from about 0.1 bar up to about 100 bar, and a transesterification catalyst concentration in the range of from about 5 ppm up to about 1000 ppm by weight.

5. A process according to claim 1, in which the liquid hourly space velocity through each of the reaction zones lies in the range of from about 0.1 hr $^{-1}$ up to about 10 hr $^{-1}$.

6. A process according to claim 1, in which the rates of supply of the dialkyl carbonates and of the aromatic hydroxy compound to the primary reaction zone are selected so as to provide therein a dialkyl carbonate:aromatic hydroxy compound molar ratio in the range of from about 5.1 to about 1.5.

7. A process according to claim 6, in which the dialkyl carbonate:aromatic hydroxy compound molar ratio is from about 0.8:1 to about 1.2:1.

8. A process according to claim 1, in which the dialkyl carbonate is dimethyl carbonate, in which the aromatic hydroxy compound is phenol, in which the alkyl aryl carbonate is methyl phenyl carbonate, and in which the diaryl carbonate is diphenyl carbonate.

9. A process according to claim 1, comprising passing the vaporous stream of step (e) and the overhead vaporous stream of step (h) to an alkyl alcohol recovery zone comprising a first distillation column and a second distillation column, in which the first distillation column is operated substantially at the transesterification pressure and the second distillation column is operated at a pressure which is lower than the transesterification pressure, and in which material of the vaporous stream of step (e) and of the overhead vaporous stream of step (h) is passed through a heat exchanger which serves as reboiler to the second distillation column.

10. A process according to claim 9, in which a mixture of alkyl alcohol and dialkyl carbonate is recovered overhead from the first distillation column, in which a liquid bottom product containing alkyl aryl carbonate, aromatic hydroxy compound and dialkyl carbonate is recovered from the first distillation column and is passed through a pressure let down valve to the second distillation column, in which a mixture containing aromatic hydroxy compound and dialkyl carbonate is recovered overhead from the second distillation column and in which a liquid bottom product containing dialkyl carbonate in admixture with alkyl aryl carbonate and aromatic hydroxy compound compared is recovered from the bottom thereof.

11. A process according to claim 10, in which the mixture recovered overhead from the second distillation column is recycled to the primary reaction zone.

12. A process according to claim 10, in which the liquid bottom product from the second distillation column is recycled to the tertiary reaction zone.

13. A process according to claim 1, in which the vaporous stream from the primary reaction zone exhibits an aromatic hydroxy compound:dialkyl carbonate molar ratio of at least about 0.25:1 up to about 0.75:1 and an alkyl aryl carbonate:dialkyl carbonate molar ratio of from about 0.001:1 up to about 0.02:1.

14. A process according to claim 1, in which the liquid stream from the primary reaction zone has an aromatic hydroxy compound:dialkyl carbonate molar ratio of from about 2:1 to about 3:1, an alkyl aryl carbonate:dialkyl carbonate molar ratio of from about 0.1:1 to about 0.25:1, and a diaryl carbonate:dialkyl carbonate molar ratio of from about 0.001:1 to about 0.06:1.

15. A process according to claim 1, in which the overhead vaporous stream from the secondary reaction zone has an alkyl alcohol:dialkyl carbonate molar ratio of from about 0.02:1 to about 0.2:1, an alkyl aryl carbonate:dialkyl carbonate molar ratio of from about 0.05:1 to about 0.3:1, an aromatic hydroxy compound:dialkyl carbonate molar ratio of from about 1:1 to about 3:1, and a diaryl carbonate:dialkyl carbonate molar ratio of from about 0.0005:1 to about 0.05:1.

16. A process according to claim 1, in which the liquid stream from the secondary reaction zone has an aromatic hydroxy compound:dialkyl carbonate molar ratio of from about 5:1 to about 10:1, an alkyl aryl carbonate:dialkyl carbonate molar ratio of from about 0.5:1 to about 2:1, and a diaryl carbonate:dialkyl carbonate molar ratio of from about 0.005:1 to about 1.25:1.

17. A process according to claim 1, in which the vaporous overhead stream recovered from the tertiary reaction zone has an alkyl alcohol:dialkyl carbonate molar ratio of from about 0.001:1 to about 0.05:1 and an aromatic hydroxy compound:dialkyl carbonate molar ratio of from about 3:1 to about 8:1.

18. A process according to claim 1, in which the liquid bottom stream from the tertiary reaction zone has an alkyl alcohol:dialkyl carbonate molar ratio of from about 0.001:1 to about 0.1:1, an alkyl aryl carbonate:dialkyl carbonate molar ratio of from about 6:1 to about 30:1, an aromatic hydroxy compound:dialkyl carbonate molar ratio of from about 15:1 to about 40:1, and a diaryl carbonate:dialkyl carbonate molar ratio of from about 5:1 to about 20:1.

19. A process according to claim 1, further comprising distilling the liquid bottom product from the tertiary reaction zone under vacuum in one or more distillation columns arranged in series for the recovery of diaryl carbonate thereform.

20. A process to claim 1, in which the transesterification catalyst comprises a tetra aryl titanate wherein the aryloxy groups in said tetra aryl titanate are derived from a phenol having a higher boiling point than said aromatic hydroxy compound.

21. A process according to claim 20, wherein said aryloxy groups comprise iso-nonylphenoxy groups.

* * * * *

UNITED STATES PATENT AND TRADEMARK OFFICE
CERTIFICATE OF CORRECTION

PATENT NO. : 5,426,207
DATED : June 20, 1995
INVENTOR(S) : George E. Harrison et al.

It is certified that error appears in the above-indentified patent and that said Letters Patent is hereby corrected as shown below:

Column 8, line 25, "N-propanol" should be -- n-propanol --; Col. 12, line 19, "Via" should be -- via --; Col. 12, after the table and before line 57, insert -- Product column 107 contains three beds of --; In the Claims: Col. 21, line 32 (claim 3), "alkyl aryl" should be -- alkyl/aryl --.

Signed and Sealed this

Twenty-first Day of November, 1995

Attest:

BRUCE LEHMAN

*Attesting Officer*  *Commissioner of Patents and Trademarks*